(12) United States Patent
Piva et al.

(10) Patent No.: US 8,722,740 B2
(45) Date of Patent: May 13, 2014

(54) SYNERGETIC COMPOSITION COMPRISING FLAVOURING SUBSTANCES AND ORGANIC ACIDS AND USE THEREOF

(75) Inventors: Andrea Piva, Bologna (IT); Maurizio Tedeschi, Reggio Emilia (IT)

(73) Assignee: Vetagro S.p.A., Reggio Emilia (IT)

( * ) Notice: Subject to any disclaimer, the term of this patent is extended or adjusted under 35 U.S.C. 154(b) by 241 days.

(21) Appl. No.: 12/671,818

(22) PCT Filed: Aug. 4, 2008

(86) PCT No.: PCT/EP2008/060239
§ 371 (c)(1),
(2), (4) Date: Mar. 19, 2010

(87) PCT Pub. No.: WO2009/019255
PCT Pub. Date: Feb. 12, 2009

(65) Prior Publication Data
US 2011/0230560 A1   Sep. 22, 2011

(30) Foreign Application Priority Data
Aug. 3, 2007   (IT) .............................. MI2007A1623

(51) Int. Cl.
*A01N 37/10*   (2006.01)
*A61K 31/19*   (2006.01)

(52) U.S. Cl.
USPC ........................... 514/568; 514/557; 514/574

(58) Field of Classification Search
None
See application file for complete search history.

(56) References Cited

U.S. PATENT DOCUMENTS

| | | | |
|---|---|---|---|
| 4,159,337 | A | 6/1979 | Rowlands |
| 5,589,158 | A | 12/1996 | Mankoo |
| 2003/0212146 | A1 | 11/2003 | Ninkov |
| 2004/0009206 | A1 | 1/2004 | Piva et al. |
| 2004/0241109 | A1 | 12/2004 | Parikh |
| 2005/0014827 | A1 | 1/2005 | Schur |
| 2007/0104765 | A1 | 5/2007 | Faltys et al. |
| 2009/0004308 | A1 | 1/2009 | Frehner et al. |

FOREIGN PATENT DOCUMENTS

| | | |
|---|---|---|
| EP | 1391155 A1 | 2/2004 |
| EP | 2042041 A2 | 4/2009 |
| WO | 9407477 A1 | 4/1994 |
| WO | 00/10529 A1 | 3/2000 |

OTHER PUBLICATIONS

Santiesteban-Lopez et al "Susceptibility of food-borne bacteria to binary combination of antimicrobials at selected aw and pH", Journal of Applied Microbiology, published online Aug. 8, 2006, p. 486-497.*

Feng Zhou et al., "Synergistic effect of thymol and carvacrol combined with chelators and organic acids against *Salmonella typhimurium*", Journal of Food Protection, Des Moines, Iowa, US, vol. 70, No. 7, Jul. 1, 2007, pp. 1704-1709, XP009109916, ISSN: 0362-028X.

Database Medline [Online], US National Library of Medicine (NLM), Bethesda, MD, US, Feb. 2007, Santiesteban-Lopez, A et al., "Susceptibility of food-borne bacteria to binary combinations of antimicrobials at selected a(w) and pH.", XP002507921, Database accession No. NLM17241355 abstract & Journal of Applied Microbiology, Feb. 2007, vol. 102, No. 2, Feb. 2007, pp. 486-497, ISSN: 1364-5072.

Abd-El-Salam, et al., "Activity and Microbiological Quality of Rennet Extracts From Fresh Vells As Affected by the Used Preservative and Storage Period", Egyptian Journal of Dairy Science, vol. 17, No. 1, 1989, pp. 75-85, XP9170123.

Alakomi Hanna-Leena, et al., "Weakening of *Salmonella* With Selected Microbial Metabolites of Berry-Derived Phenolic Compounds and Organic Acids", Journal of Agricultural and Food Chemistry, vol. 55, No. 10, May 2007, pp. 3905-3912, XP002698332.

* cited by examiner

*Primary Examiner* — Wu-Cheng Winston Shen
*Assistant Examiner* — Jean Cornet
(74) *Attorney, Agent, or Firm* — Pearne & Gordon LLP

(57) ABSTRACT

The present invention relates to a composition comprising a synergetic mixture of flavorings or flavoring substances and organic acids. Moreover, the present invention relates to the use of said composition as a preservative for animal foodstuffs and additives intended preferably for monogastric animals.

13 Claims, No Drawings

SYNERGETIC COMPOSITION COMPRISING FLAVOURING SUBSTANCES AND ORGANIC ACIDS AND USE THEREOF

TECHNICAL FIELD

The present invention relates to a composition comprising a synergetic mixture of flavourings or flavouring agents and organic acids. Moreover, the present invention relates to the use of said composition as a preservative for animal foodstuffs and additives intended preferably for monogastric animals.

BACKGROUND ART

It is known that the pH value in the gastric apparatus of monogastric animals is acidic. The pH value varies according to the specific portion of the gastrointestinal tract. For example, the stomach has a pH of 2 to 5, the duodenum has a pH of 4 to 6, the jejunum has a pH of 6 to 7, the cecum has a pH of 6 to 6.5 and, finally, the colon a pH of 6.5 to 7.

In the gastrointestinal system said acid environment provides a protective effect against the proliferation of pathogens.

It is known, however, that some pathogenic organisms are capable of developing a complex defence system which enables the cells of the pathogens themselves to survive even where the pH values fall to as low as 3.

Moreover, some bacteria, such as *Salmonella typhimurium*, may develop a system able to tolerate acids with a pH of 3 after previous exposure to a weak acid with a pH of 5.

DISCLOSURE OF THE INVENTION

In EP1391155 a composition comprising organic acids and flavouring agents is described. The composition is used to prevent pathogenic infections in the gastrointestinal tract of monogastric animals.

However, there continues to be keen interest in developing new compositions with an ability to prevent or control infections due to the presence and/or proliferation of pathogens in the gastrointestinal tract. In particular, it is important to develop compositions having an improved antibacterial effectiveness.

To this end, the Applicant proposes a composition having the characteristics as described in the appended independent claim.

Preferred embodiments of the invention are in accordance with the characteristics as described in the appended dependent claims.

For the purposes of the present invention, composition means a composition in solid form, for example a granular composition or a powder composition.

For the purposes of the present invention, Council Directive 88/388/EEC of 22 Jun. 1988 on the approximation of the laws of the Member States relating to flavourings for use in foodstuffs and to source materials for their production (published in Italy in the Official Gazette, n. L 184 of 15 Jul. 1988) is applied. The Directive in question applies to "flavourings" used or intended for use in or on foodstuffs to impart odour and/or taste, and to source materials used for the production of flavourings.

Therefore, for the purposes of the present invention:

a) "flavouring" means flavouring substances, flavouring preparations, process flavourings, smoke flavourings or mixtures thereof;

b) "flavouring substance" means a defined chemical substance with flavouring properties which is obtained i) by appropriate physical processes (including distillation and solvent extraction) or enzymatic or microbiological processes from material of vegetable or animal origin either in the raw state or after processing for human consumption by traditional food-preparation processes (including drying, torrefaction and fermentation);

ii) by chemical synthesis or isolated by chemical processes and which is chemically identical to a substance naturally present in material of vegetable or animal origin as described in i);

iii) by chemical synthesis but which is not chemically identical to a substance naturally present in material of vegetable or animal origin as described in i);

c) "flavouring preparation" means a product, other than the substances defined in b) i), whether concentrated or not, with flavouring properties, which is obtained by appropriate physical processes (including distillation and solvent extraction) or by enzymatic or microbiological processes from material of vegetable or animal origin, either in the raw state or after processing for human consumption by traditional food-preparation processes (including drying, torrefaction and fermentation);

d) "process flavouring" means a product which is obtained according to good manufacturing practices by heating to a temperature not exceeding 180° C. for a period not exceeding 15 minutes a mixture of ingredients, not necessarily themselves having flavouring properties, of which at least one contains nitrogen (amino) and another is a reducing sugar;

e) "smoke flavouring" means a smoke extract used in traditional foodstuff smoking processes.

Flavourings may contain foodstuffs as well as other substances.

The composition to which the present invention relates comprises a mixture consisting of at least one substance selected from the group as defined above in a), b), c), d) and e) in combination with at least one organic acid and/or at least one organic acid in salified form.

In one embodiment, said substance can be, for example, a flavouring or flavouring substance, without any limitation. Said substance is chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone, 1,8-cineole.

For example, p-cymene is present in *Thymus vulgaris* and *Origanum vulgare*; g-terpinene is present in *Thymus vulgaris* and *Origanum vulgare*; α-thujone is present in *Salvia officinalis*; α-pinene is present in *Rosmarinus officinalis* and *Salvia officinalis;* 1,8-cineole is present in *Rosmarinus officinalis* and *Salvia officinalis.*

The organic acid is chosen from the group comprising lactic, malic, benzoic, fumaric and sorbic acid or a salt thereof. For the purposes of the present invention, the organic acid can be present in salified form, e.g. with an alkali or alkaline-earth metal.

In a preferred embodiment, the composition moreover comprises citric acid or an alkali or alkaline-earth metal citrate.

For example, the composition may be represented by citric acid, sorbic acid and thymol.

The mixture may be in solid form or in liquid form, e.g. in aqueous solution.

In the mixture of the present invention, the molar ratio between said at least one substance as defined above in a), b), c), d) and e) and said at least one organic acid is within the range of 1:500 to 500:1, preferably 1:300 to 300:1, and even more preferably 1:200 to 200:1. Advantageously, the molar ratio is within the range of 1:150 to 150:1, for example 1:100 to 100:1, or 1:50 to 50:1, or 1:25 to 25:1.

The composition and/or mixture of the present invention may also contain other nutritional components that are useful and physiologically acceptable for animals.

The mixture in liquid form, for example in aqueous solution, can have a pH of 6.5 to 7.5. The mixture can be converted into solid form by means of a crystallization process known within the art.

In a preferred embodiment, the mixture is comprised of at least two flavourings or flavouring substances chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole and at least two organic acids chosen from the group comprising lactic acid, malic acid, benzoic acid, fumaric acid and sorbic acid. The mixture is preferably comprised of three flavourings or flavouring substances and at least three organic acids. Even more preferably, the mixture is comprised of four flavourings or flavouring substances and at least four organic acids.

In a preferred embodiment, the mixture is comprised of carvacrol and at least one organic acid chosen from the group comprising citric acid, lactic acid, malic acid, benzoic acid, fumaric acid and sorbic acid. The mixture is preferably comprised of carvacrol and at least two organic acids; even more preferably, three organic acids.

In a preferred embodiment, the mixture is comprised of thymol and at least one organic acid chosen from the group comprising lactic acid, malic acid, benzoic acid, fumaric acid and sorbic acid. The mixture is preferably comprised of thymol and at least two organic acids; even more preferably, three organic acids.

In a preferred embodiment, the mixture is comprised of cinnamaldehyde and at least one organic acid chosen from the group comprising citric acid, lactic acid, malic acid, benzoic acid, fumaric acid and sorbic acid. The mixture is preferably comprised of cinnamaldehyde and at least two organic acids; even more preferably, three organic acids.

In a preferred embodiment, the mixture is comprised of vanillin and at least one organic acid chosen from the group comprising citric acid, lactic acid, malic acid, benzoic acid, fumaric acid and sorbic acid. The mixture is preferably comprised of vanillin and at least two organic acids; even more preferably, three organic acids.

In a preferred embodiment, the mixture is comprised of camphor and at least one organic acid chosen from the group comprising citric acid, lactic acid, malic acid, benzoic acid, fumaric acid and sorbic acid. The mixture is preferably comprised of camphor and at least two organic acids; even more preferably, three organic acids.

In a preferred embodiment, the mixture is comprised of heptanoic acid and at least one organic acid chosen from the group comprising citric acid, lactic acid, malic acid, benzoic acid, fumaric acid and sorbic acid. The mixture is preferably comprised of heptanoic acid and at least two organic acids; even more preferably, three organic acids.

In a preferred embodiment, the mixture is comprised of octanoic acid and at least one organic acid chosen from the group comprising citric acid, lactic acid, malic acid, benzoic acid, fumaric acid and sorbic acid. The mixture is preferably comprised of octanoic acid and at least two organic acids; even more preferably, three organic acids.

In a preferred embodiment, the mixture is comprised of limonene and at least one organic acid chosen from the group comprising citric acid, lactic acid, malic acid, benzoic acid, fumaric acid and sorbic acid. The mixture is preferably comprised of limonene and at least two organic acids; even more preferably, three organic acids.

In a preferred embodiment, the mixture is comprised of diallyl disulfide and at least one organic acid chosen from the group comprising citric acid, lactic acid, malic acid, benzoic acid, fumaric acid and sorbic acid. The mixture is preferably comprised of diallyl disulfide and at least two organic acids; even more preferably, three organic acids.

In a preferred embodiment, the mixture is comprised of rosmarinic acid and at least one organic acid chosen from the group comprising citric acid, lactic acid, malic acid, benzoic acid, fumaric acid and sorbic acid. The mixture is preferably comprised of rosmarinic acid and at least two organic acids; even more preferably, three organic acids.

In a preferred embodiment, the mixture is comprised of α-pinene and at least one organic acid chosen from the group comprising citric acid, lactic acid, malic acid, benzoic acid, fumaric acid and sorbic acid. The mixture is preferably comprised of α-pinene and at least two organic acids; even more preferably, three organic acids.

In a preferred embodiment, the mixture is comprised of α-thujone and at least one organic acid chosen from the group comprising citric acid, lactic acid, malic acid, benzoic acid, fumaric acid and sorbic acid. The mixture is preferably comprised of α-thujone and at least two organic acids; even more preferably, three organic acids.

In a preferred embodiment, the mixture is comprised of cineole and at least one organic acid chosen from the group comprising citric acid, lactic acid, malic acid, benzoic acid, fumaric acid and sorbic acid. The mixture is preferably comprised of cineole and at least two organic acids; even more preferably, three organic acids.

In a preferred embodiment, the mixture is comprised of γ-terpinene and at least one organic acid chosen from the group comprising citric acid, lactic acid, malic acid, benzoic acid, fumaric acid and sorbic acid. The mixture is preferably comprised of γ-terpinene and at least two organic acids; even more preferably, three organic acids.

In a preferred embodiment, the mixture is comprised of p-cymene and at least one organic acid chosen from the group comprising citric acid, lactic acid, malic acid, benzoic acid, fumaric acid and sorbic acid. The mixture is preferably comprised of p-cymene and at least two organic acids; even more preferably, three organic acids.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of citric acid. The mixture is preferably comprised of two flavourings or flavouring substances and citric acid; even more preferably three flavourings or flavouring substances.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of lactic acid. The mixture is preferably comprised of two flavourings or flavouring substances and lactic acid; even more preferably three flavourings or flavouring substances.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of malic acid. The mixture is preferably comprised of two flavourings or flavouring substances and malic acid; even more preferably three flavourings or flavouring substances.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of benzoic acid. The mixture is preferably comprised of two flavourings or flavouring substances and benzoic acid; even more preferably three flavourings or flavouring substances.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of fumaric acid. The mixture is preferably comprised of two flavourings or flavouring substances and fumaric acid; even more preferably three flavourings or flavouring substances.

In a preferred embodiment, the mixture is comprised of at least one flavouring or flavouring substance chosen from the group comprising thymol, vanillin, carvacrol, cinnamaldehyde, octanoic acid, heptanoic acid, diallyl disulfide, camphor, limonene, rosmarinic acid, p-cymene, γ-terpinene, α-pinene, α-thujone and 1,8-cineole, and of sorbic acid. The mixture is preferably comprised of two flavourings or flavouring substances and sorbic acid; even more preferably three flavourings or flavouring substances.

Advantageously, the molar ratio between said at least one flavouring or flavouring substance and said at least one organic acid is within the range of 1:300 to 1:5 for malic acid or lactic acid respectively; preferably from 1:100 to 1:10.

Advantageously, the molar ratio between said at least one flavouring or flavouring substance and said at least one organic acid is within the range of 1:250 to 1:5 for benzoic acid or citric acid respectively; preferably 1:100 to 1:10.

Advantageously, the molar ratio between said at least one flavouring or flavouring substance and said at least one organic acid is within the range of 1:250 to 1:5 for fumaric acid; preferably 1:125 to 1:10.

Advantageously, the molar ratio between said at least one flavouring or flavouring substance and said at least one organic acid is within the range of 1:100 to 1:5 for sorbic acid; preferably 1:50 to 1:10.

Advantageously, the mixture comprised of thymol, carvacrol and cinnamaldehyde provides a noteworthy antibacterial action and enables any pathogens present to be considerably reduced/eliminated after only 24 hours.

It is an object of the present invention to provide a composition comprising a mixture as described above, which is coated by a layer of a delivery agent. Said delivery agent is chosen from among those which can deliver and release the components of said mixture in the gastrointestinal tract. The release in different portions of the gastrointestinal tract is a function of time, temperature, pH and the bacterial flora and micro-organisms present therein.

Preferably, the mixture of the invention has an external coating that comprises two distinct layers. The coating is able to release the components present in the mixture as a function of time, temperature, pH and the bacterial flora and micro-organisms present in different portions of the gastrointestinal tract.

The mixture may be coated by one or two layers using techniques known to the person skilled in the art.

Alternatively, the delivery agent may be mixed with said at least one flavouring or flavouring substance and said at least one organic acid. The mixture of the components may be achieved using techniques known to the person skilled in the art.

One example of a procedure provides for the delivery agent, for example a vegetable triglyceride, to be introduced into a container equipped with heating and mixing devices. The container temperature is subsequently brought to a temperature of 80 to 120° C. and the matrix is kept under stirring until the delivery agent melts. Optionally, additives may later be added to the melted matrix. The stirring and temperature are maintained until a mass of delivery agent with a homogenous distribution of additives is obtained. During this stage emulsifiers may be added to said mass.

The coated or uncoated composition can be converted into granular form using techniques known to the person skilled in the art.

The delivery agent may comprise a lipid substance having the ability to modulate a slow release of the components of the mixture.

It is important for the components of the mixture to be released gradually into the different portions of the gastrointestinal tract. A gradual and specific release into the different portions of the gastrointestinal tract serves to improve the antibacterial activity of the composition of the present invention, since a better synergy among the components of the mixture is achieved.

The lipid substance is chosen among hydrogenated and/or non-hydrogenated triglycerides. The triglycerides are chosen among those of vegetable and/or animal origin.

Hydrogenated vegetable triglycerides are chosen from the group comprising: palm oil, sunflower oil, corn oil, rape oil, peanut oil and soybean oil.

Triglycerides of animal origin are chosen among: bovine tallow and swine lard.

Preferably, the composition may comprise the delivery agent in an amount of 40 to 70% by weight; for example in an amount of 45 to 55% by weight, and the mixture, according to the invention, in an amount of 1 to 50% by weight; for example in an amount of 5 to 40% by weight or of 15 to 30% by weight, in proportion to the total weight of the composition.

The matrix may also comprise particular additives. The additives are chosen from the group comprising: fumed silica, calcium stearate, magnesium stearate and calcium sulfate. The additives used serve to increase the viscosity of the matrix itself and reduce its permeability. Preferably, the delivery agent comprises several additives in an amount of 0.1 to 30% by weight, in proportion to the total weight of the delivery agent; for example 1 to 20% or 5 to 10% by weight.

The composition of the invention can be used for preventing and/or treating bacterial infections. For the purposes of the present invention, bacterial infections means all situations where the presence and/or growth of prokaryote organisms have a detrimental effect on the host, such as causing a disease.

Among said prokaryote organisms mention shall be made of those belonging to the species: *Salmonella* sp., *S. aureus*, *E. faecalis*, *E. coli*, *K. Pneumoniae*, *P. mirabilis*, *P. aeruginosa*, *C. perfrigens*, *Cambylobacter* sp., *S. pneumoniae*, *B. cereus*, *C. albicans*, *A. oryzae*, *P. funiculosum* and *F. moniliforme*.

In a more preferred embodiment, said prokaryote organisms are *C. Perfrigens* and *Salmonella typhimurium*. In another preferred embodiment, said mixture is used to prepare a medication for preventing and/or treating bacterial infections which moreover includes a delivery agent. In an even more preferable embodiment, said delivery agent is a lipid matrix as described above.

The medication in said embodiment can be used for preventing and/or treating bacterial infections in the gastrointestinal system of monogastric animals.

The composition of the present invention finds application as a preservative for animal foodstuffs and additives.

Experimental Part

EXAMPLE 1

Evaluation of the Antimicrobial Activity Exerted by Organic Acids and Flavourings or Flavouring Substances Against *Clostridium perfringens* After 24 Hours of Incubation in Microtitration Plates, Using the Optical Density Method Practically speaking, the antibacterial power of the mixtures of the present invention was determined using a dilution method and optical density measurements (Smith-Palmer et al.; 1998).

The minimum inhibitory concentration (MIC) of a substance or mixture can be defined as the lowest concentration of that substance or mixture which will inhibit the growth of organisms used at a particular infection dose after a certain amount of time (Karapinar and Aktug, 1987; Onawunmi, 1989; Hammer et al., 1999; Delaquis et al., 2002).

*C. perfringens* was preserved in cooked meat at room temperature, inoculated into a culture broth (Oxoid) containing RCM (Reinforced Clostridial Medium) and incubated at 37° C. for 24 hours under anaerobiosis.

Before being used, the preserved strains of *C. perfringens* were cultured twice, each time by 24 h incubation.

The following flavourings or flavouring substances were tested: thymol, vanillin, carvacrol, cinnamaldehyde, heptanoic acid, octanoic acid, camphor, limonene, diallyl disulfide, rosmarinic acid, α-pinene, α-thujone, cineole, γ-terpinene and p-cymene.

The following organic acids were tested: citric acid, sorbic acid, malic acid, fumaric acid, benzoic acid and lactic acid.

The stock solutions of each of the above-named substances (flavourings/flavouring substances and organic acids) were prepared by dissolving said substances in deionised water. The pH of the solution was corrected to 6.5 and the solution was subsequently submitted to sterile filtration (pore diameter 0.22 μm).

The working solutions containing the organic acid were prepared by carrying out a two-fold serial dilution of each stock solution using a culture broth prepared as described above, with a pH of 6.5, in order to obtain the lowest concentrations to be tested according to the type of acid.

The flavour stock solutions were obtained by diluting the solutions in ethyl alcohol (75%) in order to reach 7.28 mm, but the stock solutions for vanillin, limonene and camphor were obtained using deionised water.

The pH of all solutions was adjusted to around 6.5. All solutions were sterilised by filtration using pores with a diameter of 0.22 μm.

The working solutions containing the culture broth and flavourings or flavouring substances were prepared by diluting the latter with the culture broth RMC at a pH of 6.5 (stock solution containing flavourings or flavouring substances: RMC broth=3:1). The other concentrations, up to 1.96 mM, were obtained in the same way.

The inhibition of *Clostridium perfringens* was analysed at a concentration of $1\times10^4$ CPU per well. Each of the 96 wells was filled with 100 μl of bacterial inoculum ($1\times10^5$ CFU/ml) and 100 μl of each solution. The negative control wells were inoculated in the same manner with 100 μl of culture ($1\times10^5$ CFU/ml) and 100 μl of culture broth (pH 6.5) without the addition of any substance (organic acid or flavouring substance). Each substance was tested twice per plate.

The plates of *Clostridium perfringens* were incubated at 37° C. under anaerobic conditions.

The turbidity of the cultures was used as an indicator of bacterial growth and was assessed by measuring absorbance at 630 nm (Tecan Spectra Classic). Absorbance was measured after 24 hours' incubation.

Results

An analysis of the graphs depicting the growth of *Clostridium perfringens*, as determined on the basis of absorbance measurements, shows an improved/increased antibacterial activity for the mixtures listed below, compared to the activity of each organic acid or flavouring substance considered on its own.

The mixtures displaying a synergetic effect between the organic acid and flavouring substance used, as compared to the organic substance considered individually or the flavouring substance considered individually, are listed below:

1. carvacrol 0.98-0.49+citric acid 31.25-7.82.
Hence, carvacrol and citric acid are preferably used in a molar ratio of about 1:5 to 1:65.
2. carvacrol 0.98-0.49+sorbic acid 50-3.13.
Hence, carvacrol and sorbic acid are preferably used in a molar ratio of about 1:3 to 1:110.
3. carvacrol 0.98-0.49+malic acid 125-15.63.
Hence, carvacrol and malic acid are preferably used in a molar ratio of about 1:10 to 1:260.
4. carvacrol 0.98+fumaric acid 62.5-7.82.
Hence, carvacrol and fumaric acid are preferably used in a molar ratio of about 1:5 to 1:65.
5. carvacrol 0.98+benzoic acid 62.5-31.25.
Hence, carvacrol and benzoic acid are preferably used in a molar ratio of about 1:30 to 1:75.
6. carvacrol 0.98-0.73+lactic acid 125-62.5.
Hence, carvacrol and lactic acid are preferably used in a molar ratio of about 1:60 to 1:180.
7. thymol 1.46-0.49+citric acid 31.25-15.63.
Hence, thymol and citric acid are preferably used in a molar ratio of about 1:10 to 1:75.
8. thymol 0.98+sorbic acid 25-6.25.
Hence, thymol and sorbic acid are preferably used in a molar ratio of about 1:5 to 1:30.
9. thymol 0.98-0.73+malic acid 125-31.25.
Hence, thymol and malic acid are preferably used in a molar ratio of about 1:30 to 1:180.
10. thymol 1.82-0.98+fumaric acid 125-31.25.
Hence, thymol and fumaric acid are preferably used in a molar ratio of about 1:10 to 1:150.
11. thymol 0.98-0.73+benzoic acid 62.5-15.63.
Hence, thymol and benzoic acid are preferably used in a molar ratio of about 1:10 to 1:90.
12. thymol 0.98+lactic acid 500.
Hence, thymol and lactic acid are preferably used in a molar ratio of about 1:450 to 1:550.
13. cinnamaldehyde 0.98-0.49+citric acid 15.63-7.82.
Hence, cinnamaldehyde and citric acid are preferably used in a molar ratio of about 1:5 to 1:35.
14. cinnamaldehyde 1.46-0.49+sorbic acid 50-3.13.
Hence, cinnamaldehyde and sorbic acid are preferably used in a molar ratio of about 1:2 to 1:110.

15. cinnamaldehyde 0.49+malic acid 62.5-15.63.

Hence, cinnamaldehyde and malic acid are preferably used in a molar ratio of about 1:30 to 1:135.

16. cinnamaldehyde 0.98+fumaric acid 62.5-15.63.

Hence, cinnamaldehyde and fumaric acid are preferably used in a molar ratio of about 1:10 to 1:65.

17. cinnamaldehyde 0.98-0.73+benzoic acid 31.25-7.62.

Hence, cinnamaldehyde and benzoic citric acid are preferably used in a molar ratio of about 1:5 to 1:50.

18. cinnamaldehyde 1.46-0.98+lactic acid 125-62.5.

Hence, cinnamaldehyde and lactic acid are preferably used in a molar ratio of about 1:40 to 1:135.

19. vanillin 1.82-0.49+citric acid 31.25.

Hence, vanillin and citric acid are preferably used in a molar ratio of about 1:10 to 1:70.

20. vanillin 1.82-0.98+sorbic acid 50-25.

Hence, vanillin and sorbic acid are preferably used in a molar ratio of about 1:10 to 1:60.

21. vanillin 1.46+malic acid 125.

Hence, vanillin and malic acid are preferably used in a molar ratio of about 1:80 to 1:100.

22. vanillin 1.82-0.73+fumaric acid 31.25-3.91.

Hence, vanillin and fumaric acid are preferably used in a molar ratio of about 1:2 to 1:50.

23. vanillin 0.73-0.49+benzoic acid 62.5.

Hence, vanillin and benzoic acid are preferably used in a molar ratio of about 1:80 to 1:130.

24. vanillin 1.82-0.98+lactic acid 500-250.

Hence, vanillin and lactic acid are preferably used in a molar ratio of about 1:100 to 1:600.

25. camphor 0.98-0.49+citric acid 31.25.

Hence, camphor and citric acid are preferably used in a molar ratio of about 1:30 to 1:70.

26. camphor 0.98+sorbic acid 25.

Hence, camphor and sorbic acid are preferably used in a molar ratio of about 1:20 to 1:40.

27. camphor 1.46+malic acid 250.

Hence, camphor and malic acid are preferably used in a molar ratio of about 1:150 to 1:200.

28. camphor 1.82 to 1.46+fumaric acid 125-62.5.

Hence, camphor and fumaric acid are preferably used in a molar ratio of about 1:30 to 1:100.

29. camphor 1.82+benzoic acid 62.5.

Hence, camphor and benzoic acid are preferably used in a molar ratio of about 1:30 to 1:40.

30. camphor 1.82 to 0.98+lactic acid 500.

Hence, camphor and lactic acid are preferably used in a molar ratio of about 1:250 to 1:600.

31. heptanoic acid 1.82-0.49+citric acid 31.25-7.82.

Hence, heptanoic acid and citric acid are preferably used in a molar ratio of about 1:4 to 1:70.

32. heptanoic acid 1.82-0.73+sorbic acid 50-3.13.

Hence, heptanoic acid and sorbic acid are preferably used in a molar ratio of about 1:1 to 1:70.

33. heptanoic acid 1.82-0.73+benzoic acid 62.5-7.82.

Hence, heptanoic acid and benzoic acid are preferably used in a molar ratio of about 1:4 to 1:100.

34. heptanoic acid 1.82-0.73+lactic acid 250-31.25.

Hence, heptanoic acid and lactic acid are preferably used in a molar ratio of about 1:10 to 1:400.

35. octanoic acid 1.82-0.49+citric acid 31.25.

Hence, octanoic acid and citric acid are preferably used in a molar ratio of about 1:10 to 1:70.

36. octanoic acid 1.82-0.49+sorbic acid 50.

Hence, octanoic acid and sorbic acid are preferably used in a molar ratio of about 1:20 to 1:120.

37. octanoic acid 1.82-1.46+malic acid 250.

Hence, octanoic acid and malic acid are preferably used in a molar ratio of about 1:100 to 1:200.

38. octanoic acid 0.73+fumaric acid 7.82.

Hence, octanoic acid and fumaric acid are preferably used in a molar ratio of about 1:10 to 1:15.

39. octanoic acid 1.82-0.73+benzoic acid 62.5.

Hence, octanoic acid and benzoic acid are preferably used in a molar ratio of about 1:30 to 1:200.

40. octanoic acid 1.82+lactic acid 250.

Hence, octanoic acid and lactic acid are preferably used in a molar ratio of about 1:100 to 1:150.

41. limonene 1.82-0.73+citric acid 31.25.

Hence, limonene acid and citric acid are preferably used in a molar ratio of about 1:10 to 1:50.

42. limonene 1.82-0.98+sorbic acid 50.

Hence, limonene acid and sorbic acid are preferably used in a molar ratio of about 1:20 to 1:60.

43. limonene 1.82-0.49+malic acid 250.

Hence, limonene acid and malic acid are preferably used in a molar ratio of about 1:100 to 1:600.

44. limonene 1.82-1.46+benzoic acid 62.5.

Hence, limonene and benzoic acid are preferably used in a molar ratio of about 1:30 to 1:50.

45. limonene 1.82+lactic acid 500.

Hence, limonene acid and lactic acid are preferably used in a molar ratio of about 1:250 to 1:300.

46. diallyl disulfide 1.82-0.49+citric acid 31.25-7.82.

Hence, diallyl disulfide and citric acid are preferably used in a molar ratio of about 1:4 to 1:70.

47. diallyl disulfide 1.82-0.73+sorbic acid 50-3.13.

Hence, diallyl disulfide and sorbic acid are preferably used in a molar ratio of about 1:1 to 1:70.

48. diallyl disulfide 1.82-0.98+malic acid 250-62.5.

Hence, diallyl disulfide and malic acid are preferably used in a molar ratio of about 1:30 to 1:270.

49. diallyl disulfide 1.82-0.98+benzoic acid 62.5-15.63.

Hence, diallyl disulfide and benzoic acid are preferably used in a molar ratio of about 1:5 to 1:70.

50. diallyl disulfide 1.82-0.73+lactic acid 500-15.63.

Hence, diallyl disulfide and lactic acid are preferably used in a molar ratio of about 1:5 to 1:700.

51. rosmarinic acid 0.98+citric acid 31.25.

Hence, rosmarinic acid and citric acid are preferably used in a molar ratio of about 1:30 to 1:40.

52. rosmarinic acid 1.46+sorbic acid 12.5.

Hence, rosmarinic acid and sorbic acid are preferably used in a molar ratio of about 1:5 to 1:15.

53. rosmarinic acid 0.98+malic acid 62.5.

Hence, rosmarinic acid and malic acid are preferably used in a molar ratio of about 1:50 to 1:100.

54. rosmarinic acid 1.82-0.98+fumaric acid 62.5.

Hence, rosmarinic acid and fumaric acid are preferably used in a molar ratio of about 1:30 to 1:80.

55. rosmarinic acid 1.82-0.73+benzoic acid 15.63.

Hence, rosmarinic acid and benzoic acid are preferably used in a molar ratio of about 1:5 to 1:30.

56. rosmarinic acid 1.82-0.49+lactic acid 125-62.5.

Hence, rosmarinic acid and lactic acid are preferably used in a molar ratio of about 1:30 to 1:300.

57. α-pinene 1.46-0.73+citric acid 31.25-7.82.

Hence, α-pinene and citric acid are preferably used in a molar ratio of about 1:5 to 1:50.

58. α-pinene 0.98-0.73+sorbic acid 50-1.56.

Hence, α-pinene and sorbic acid are preferably used in a molar ratio of about 1:1 to 1:80.

59. α-pinene 1.46-0.49+malic acid 250-15.63.

Hence, α-pinene and malic acid are preferably used in a molar ratio of about 1:10 to 1:600.

60. α-pinene 1.46-0.49+fumaric acid 125-3.91.

Hence, α-pinene and fumaric acid are preferably used in a molar ratio of about 1:2 to 1:300.

61. α-pinene 1.46-0.49+benzoic acid 62.5-7.82.

Hence, α-pinene and benzoic acid are preferably used in a molar ratio of about 1:5 to 1:150.

62. α-pinene 1.46-0.49+lactic acid 500-15.63.

Hence, α-pinene and lactic acid are preferably used in a molar ratio of about 1:10 to 1:1200.

63. α-thujone 1.82-0.73+citric acid 31.25-7.82.

Hence, α-thujone and citric acid are preferably used in a molar ratio of about 1:4 to 1:50.

64. α-thujone 1.82-0.49+sorbic acid 50-3.13.

Hence, α-thujone and citric sorbic are preferably used in a molar ratio of about 1:1 to 1:120.

65. α-thujone 1.82-0.73+malic acid 250-15.63.

Hence, α-thujone and malic acid are preferably used in a molar ratio of about 1:5 to 1:400.

66. α-thujone 1.82-0.98+fumaric acid 125-3.91.

Hence, α-thujone and fumaric acid are preferably used in a molar ratio of about 1:2 to 1:150.

67. α-thujone 1.46-0.49+benzoic acid 62.5-15.63.

Hence, α-thujone and benzoic acid are preferably used in a molar ratio of about 1:10 to 1:150.

68. α-thujone 1.46-0.49+lactic acid 500-31.25.

Hence, α-thujone and lactic acid are preferably used in a molar ratio of about 1:20 to 1:1200.

69. cineole 1.82-0.98+citric acid 31.25-7.82.

Hence, cineole and citric acid are preferably used in a molar ratio of about 1:4 to 1:40.

70. cineole 1.82-0.73+sorbic acid 50-1.56.

Hence, cineole and sorbic acid are preferably used in a molar ratio of about 1:0.5 to 1:70.

71. cineole 1.82-0.98+malic acid 250-15.63.

Hence, cineole and malic acid are preferably used in a molar ratio of about 1:5 to 1:300.

72. cineole 1.82-1.46+fumaric acid 62.5-7.82.

Hence, cineole and fumaric acid are preferably used in a molar ratio of about 1:4 to 1:50.

73. cineole 1.82-0.49+benzoic acid 62.5-7.82.

Hence, cineole and benzoic acid are preferably used in a molar ratio of about 1:4 to 1:150.

74. cineole 1.82-0.73+lactic acid 250-7.82.

Hence, cineole and lactic acid are preferably used in a molar ratio of about 1:4 to 1:350.

75. γ-terpinene 1.82-0.49+sorbic acid 50-6.25.

Hence, γ-terpinene and sorbic acid are preferably used in a molar ratio of about 1:2 to 1:120.

76. γ-terpinene 1.82-1.46+malic acid 250-62.5.

Hence, γ-terpinene and malic acid are preferably used in a molar ratio of about 1:30 to 1:200.

77. γ-terpinene 1.82-0.49+benzoic acid 62.5-7.82.

Hence, γ-terpinene and benzoic acid are preferably used in a molar ratio of about 1:4 to 1:150.

78. γ-terpinene 1.82-0.73+lactic acid 500-15.63.

Hence, γ-terpinene and lactic acid are preferably used in a molar ratio of about 1:5 to 1:700.

79. p-cymene 1.82-0.49+sorbic acid 50-12.5.

Hence, p-cymene and sorbic acid are preferably used in a molar ratio of about 1:5 to 1:120.

80. p-cymene 1.82-0.49+benzoic acid 62.5-7.82.

Hence, p-cymene and benzoic acid are preferably used in a molar ratio of about 1:4 to 1:130.

81. p-cymene 1.82-0.49+lactic acid 500-15.63.

Hence, p-cymene and benzoic acid are preferably used in a molar ratio of about 1:5 to 1:1150.

The invention claimed is:

1. A composition comprising a mixture of (a) thymol, (b) sorbic acid or an alkali or alkaline-earth metal salt thereof, and (c) citric acid or an alkali or alkaline-earth metal salt thereof.

2. The composition according to claim 1, wherein the molar ratio between said thymol and said sorbic acid or alkali or alkaline-earth metal salt thereof is within the range of 1:500 to 500:1.

3. The composition according to claim 2, wherein the molar ratio is within the range of 1:150 to 150:1.

4. The composition according to claim 3, wherein the molar ratio is within the range of 1:100 to 1:5.

5. The composition according to claim 1, wherein said composition comprises a delivery agent.

6. The composition according to claim 5, wherein the delivery agent comprises hydrogenated and/or non-hydrogenated triglycerides of animal and/or vegetable origin.

7. Method for preparing a composition according to claim 5, which comprises at least one phase wherein the thymol and the sorbic acid or alkali or alkaline-earth metal salt thereof are added to the delivery agent in a melted state.

8. A method of using a composition according to claim 1, comprising a step of adding to an animal feed or an animal premix for feeding a monogastric animal an amount of said composition effective to reduce or prevent the development and/or proliferation of pathogenic bacteria and/or fungi in said feed or said premix.

9. A method of using a composition according to claim 1 for preparing a foodstuff to be used in the zootechnical and veterinary field, comprising a step of adding to said foodstuff an amount of said composition effective to reduce or prevent the development and/or proliferation of pathogenic bacteria and fungi in the gastro-resistant system of an animal.

10. The composition according to claim 1, wherein the molar ratio between said thymol and said sorbic acid or alkali or alkaline-earth metal salt thereof is within the range of 1:300 to 300:1.

11. The composition according to claim 1, wherein the molar ratio between said thymol and said sorbic acid or alkali or alkaline-earth metal salt thereof is within the range of 1:200 to 200:1.

12. The composition according to claim 2, wherein the molar ratio is within the range of 1:100 to 100:1.

13. The composition according to claim 2, wherein the molar ratio is within the range of 1:50 to 1:10.

* * * * *

UNITED STATES PATENT AND TRADEMARK OFFICE
CERTIFICATE OF CORRECTION

PATENT NO. : 8,722,740 B2  
APPLICATION NO. : 12/671818  
DATED : May 13, 2014  
INVENTOR(S) : Piva et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 255 days.

Signed and Sealed this
Twenty-ninth Day of September, 2015

Michelle K. Lee
*Director of the United States Patent and Trademark Office*